(12) United States Patent
Larkin

(10) Patent No.: US 8,251,918 B2
(45) Date of Patent: Aug. 28, 2012

(54) METHOD AND APPARATUS FOR SIMULTANEOUSLY COLLECTING EXOCERVICAL AND ENDOCERVICAL SAMPLES

(76) Inventor: Daniel Larkin, St. Paul, MN (US)

(*) Notice: Subject to any disclaimer, the term of this patent is extended or adjusted under 35 U.S.C. 154(b) by 0 days.

(21) Appl. No.: 12/815,147

(22) Filed: Jun. 14, 2010

(65) Prior Publication Data

US 2010/0305472 A1    Dec. 2, 2010

Related U.S. Application Data

(62) Division of application No. 11/588,120, filed on Oct. 26, 2006, now Pat. No. 7,749,173.

(60) Provisional application No. 60/810,055, filed on Jun. 1, 2006.

(51) Int. Cl.
*A61B 10/00*   (2006.01)

(52) U.S. Cl. ......... 600/569; 600/562; 600/570; 600/572

(58) Field of Classification Search .................. 600/562, 600/570, 572
See application file for complete search history.

(56) References Cited

U.S. PATENT DOCUMENTS

| | | |
|---|---|---|
| 2,601,513 A | 6/1952 | Gladstone |
| 2,701,559 A | 2/1955 | Cooper |
| 2,763,104 A | 9/1956 | Lindenborg |
| 2,767,703 A | 10/1956 | Nieburgs |
| 3,815,580 A | 6/1974 | Oster |
| 3,838,681 A | 10/1974 | Dalton |
| 3,877,464 A | 4/1975 | Vermes |
| 4,027,658 A | 6/1977 | Marshall |
| 4,127,113 A | 11/1978 | Nollan |
| 4,227,537 A | 10/1980 | Suciu et al. |
| 4,700,713 A | 10/1987 | Kist |
| 4,754,764 A | 7/1988 | Bayne |
| 4,759,376 A * | 7/1988 | Stormby ..................... 600/569 |
| 4,762,133 A | 8/1988 | Bayne et al. |
| 4,981,143 A | 1/1991 | Sakita et al. |
| D316,488 S | 4/1991 | Stormby |
| 5,022,408 A | 6/1991 | Mohajer |
| 5,084,005 A | 1/1992 | Kachigian |
| 5,131,402 A | 7/1992 | Van Dooren |
| 5,191,899 A | 3/1993 | Strickland et al. |
| D335,706 S | 5/1993 | Mohajer |
| 5,253,652 A | 10/1993 | Fast |
| 5,279,307 A | 1/1994 | Mohajer |

(Continued)

FOREIGN PATENT DOCUMENTS

EP    0 448 137 A1    9/1991

(Continued)

*Primary Examiner* — Sean Dougherty
(74) *Attorney, Agent, or Firm* — Dicke, Billig & Czaja, PLLC

(57) ABSTRACT

A method of simultaneously collecting exocervical and endocervical cells from a female patient, includes providing a combination exo-endocervical sampling device including a sampler having a pair of opposing wings and a prominence extending from the wings. The opposing wings include a sampling surface and the prominence includes a multiplicity of endless looped fiber pairs distributed axially along a distal end section of the prominence. Each looped fiber pair includes a first loop extending transverse from the shaft and a second loop extending transverse from the shaft. The loops define a void space therebetween configured to capture exo-endocervical cells. The method includes placing the sampling device in contact with a cervix of the female patient, collecting exocervical cells with the opposing wings of the sampling device, and simultaneously collecting endocervical cells with the prominence.

3 Claims, 8 Drawing Sheets

U.S. PATENT DOCUMENTS

| | | | |
|---|---|---|---|
| 5,370,128 A | 12/1994 | Wainwright |
| 5,445,164 A | 8/1995 | Worthen et al. |
| 5,476,104 A | 12/1995 | Sheahon |
| 5,535,756 A | 7/1996 | Parasher |
| 5,623,941 A | 4/1997 | Hedberg et al. |
| 5,713,369 A | 2/1998 | Tao et al. |
| 5,722,423 A | 3/1998 | Lind et al. |
| 5,787,891 A | 8/1998 | Sak |
| 5,873,992 A | 2/1999 | Glezen et al. |
| 6,013,036 A | 1/2000 | Caillouette |
| 6,099,539 A | 8/2000 | Howell et al. |
| D441,141 S | 4/2001 | Shalita |
| 6,258,044 B1 | 7/2001 | Lonky et al. |
| 6,277,089 B1 | 8/2001 | Yoon |
| 6,346,086 B1 | 2/2002 | Maksem et al. |
| 6,394,966 B1 | 5/2002 | Gill et al. |
| 6,409,681 B1 | 6/2002 | Caillouette |
| 6,612,996 B2 | 9/2003 | Williams |
| 6,623,440 B1 | 9/2003 | Weldon |
| 6,723,057 B1 | 4/2004 | Pearce |
| 6,749,575 B2 | 6/2004 | Matriano et al. |
| D500,410 S | 1/2005 | Dragan |
| D500,553 S | 1/2005 | George |
| 7,097,629 B2 | 8/2006 | Blair |
| 7,226,457 B2 | 6/2007 | Carson et al. |
| 7,413,551 B2 * | 8/2008 | Decker et al. ............ 600/569 |
| 7,749,173 B2 * | 7/2010 | Larkin ...................... 600/569 |
| 2002/0032389 A1 | 3/2002 | Fournier |
| 2002/0068881 A1 | 6/2002 | Kobren et al. |
| 2004/0015300 A1 | 1/2004 | Ganguli et al. |
| 2004/0236247 A1 | 11/2004 | Rizvi |
| 2005/0159721 A1 | 7/2005 | Yamamoto et al. |
| 2005/0283129 A1 | 12/2005 | Hammons et al. |
| 2006/0142668 A1 | 6/2006 | Triva |
| 2006/0161076 A1 | 7/2006 | Gombrich et al. |
| 2007/0073186 A1 | 3/2007 | Decker et al. |

FOREIGN PATENT DOCUMENTS

| | | |
|---|---|---|
| GB | 2 208 603 A | 4/1989 |
| WO | 91/16855 A1 | 11/1991 |
| WO | 99/53841 A1 | 10/1999 |

\* cited by examiner

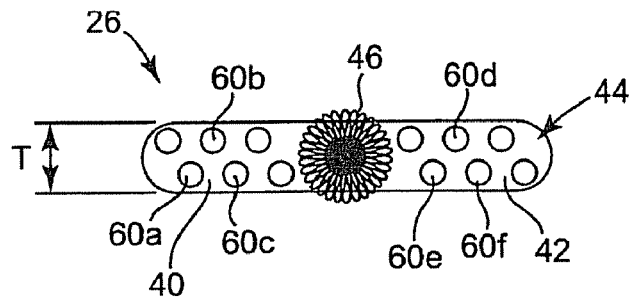
Fig. 1C
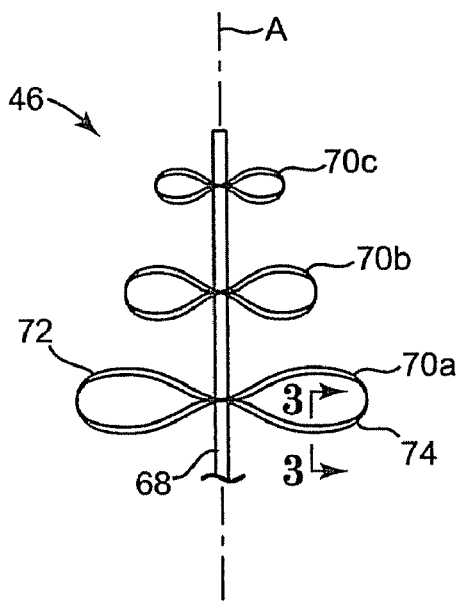
Fig. 2
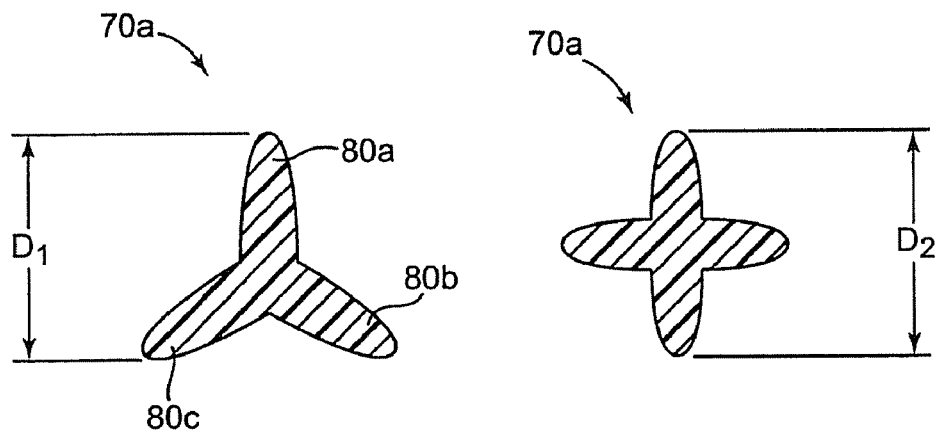
Fig. 3A    Fig. 3B

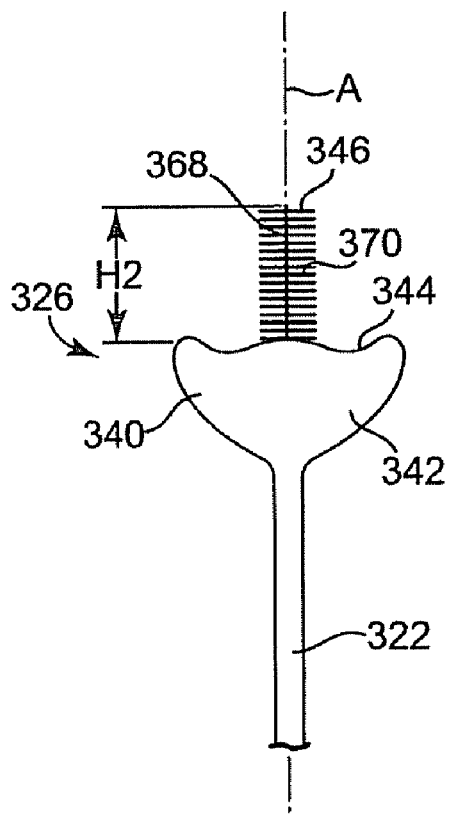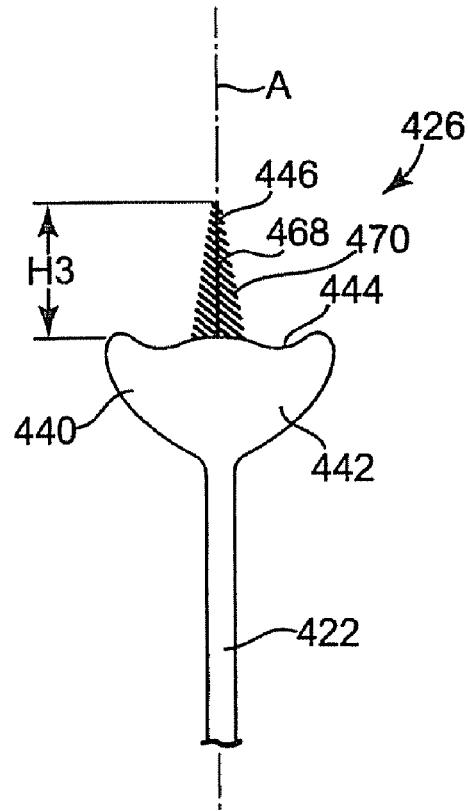
Fig. 6         Fig. 7
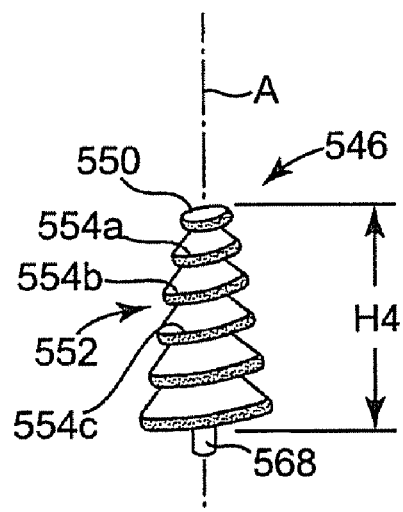
Fig. 8

METHOD AND APPARATUS FOR SIMULTANEOUSLY COLLECTING EXOCERVICAL AND ENDOCERVICAL SAMPLES

CROSS-REFERENCE TO RELATED APPLICATIONS

This application is a divisional of U.S. application Ser. No. 11/588,120, filed Oct. 26, 2006, entitled "Method and Apparatus for Simultaneously Collecting Exocervical and Endocervical Samples", which claims the benefit of the filing date of U.S. Provisional Patent Application Ser. No. 60/810,055, filed Jun. 1, 2006, entitled "Method and Apparatus for Simultaneously Collecting Exocervical And Endocervical Samples"; all of which are incorporated herein by reference

BACKGROUND

The Papanicolaou test ("Pap test" or Pap smear) has proven to be highly valuable in the early detection of cervical pre-cancerous and cancerous growths. The Pap test refers to the collection of cells from the cervical face, the endocervical canal, and occasionally from the vaginal wall. The collected cells are subsequently "smeared" onto a microscope plate or deposited and mixed into a broth and analyzed for evidence of pre-cancerous or cancerous growth. A periodic Pap test permits the early detection of malignant cells, which enables early palliative care in treating cervical pre-cancerous and cancerous growths.

One device that has been useful in collecting cells during a Pap test includes a wooden or plastic spatula. Such spatulas are inexpensive and can be effective at collecting cells from the cervical face. However, spatulas have proven to be less than effective in collecting adequate cell samples from the endocervical canal. This is a potentially serious short-coming, because any sample that does not include endocervical cells is deemed to be an inadequate Pap smear sample. That is to say, the proper interpretation and diagnosis of the state of the cells is inconclusive unless a sufficient number of cells are collected from the endocervical canal.

Other devices that are useful in collecting cells during Pap tests include cotton swabs and the like. In general, cell samples are collected by swabbing the exocervical wall and the endocervical canal with the swab. Although cotton swabs are associated with a somewhat improved collection/yield of cells, cotton swabs are not abrasive enough to scrap the endocervical canal and consistently retrieve an adequate, representative sample.

Certain bristle brushes have also proven useful in collecting cells during a Pap test. In this regard, the bristle brushes are capable of obtaining endocervical cells during sampling, however bristle brushes are abrasive, and their use can be uncomfortable and increase the incidence of patient bleeding.

Pap tests have proven to be useful in the early detection of malignant cells and are related to a reduction in the incidence and death rate due to cervical cancers. Improvements to sampling devices useful in collecting cells during Pap tests will be welcomed by the medical community and patients alike.

SUMMARY

One embodiment provides a combination exo-endocervical sampling device that includes a shaft, a sampler, and a combination exo-endocervical sampler. The shaft defines a first end opposite a second end, a transverse break line between the first and second ends, and a textured surface adjacent to the break line. The sampler is coupled to the first end, and the combination exo-endocervical sampler is coupled to the second end. The combination exo-endocervical sampler includes a pair of opposing wings disposed transverse to the shaft, and a brush that extends from the wings along a central axis of the shaft. In this regard, each of the opposing wings includes a sampling surface having a staggered array of beads, and the brush includes a multiplicity of looped fibers, where each looped fiber includes a first closed end opposite a second closed end such that the closed ends extend transverse from the central axis of the shaft.

Another embodiment of the present invention provides a combination exo-endocervical sampling device that includes a shaft, and a combination exo-endocervical sampler coupled to the shaft. The combination exo-endocervical sampler includes a pair of opposing wings disposed transverse to the shaft and a prominence extending from the wings along a central axis of the shaft. In this regard, the opposing wings define a first sampling surface and the prominence includes a second sampling surface, at least one of the first and second sampling surfaces characterized by an absence of bristles and defining a void space configured to capture exo-endocervical cells.

Another embodiment of the present invention provides a combination exo-endocervical sampling device. The device includes a shaft, a sampler coupled to an end of the shaft, and a combination exo-endocervical sampler coupled to another end of the shaft. The shaft defines a transverse break line between the ends, and a textured surface adjacent to the break line. The sampler includes one of a swab or a spatula. The combination exo-endocervical sampler includes a pair of opposing wings disposed transverse to the shaft and a prominence extending from the wings along a central axis of the shaft. In this regard, the opposing wings define a first sampling surface and the prominence includes a second sampling surface, at least one of the first and second sampling surfaces including a multiplicity of endless fibrils defining a void space therebetween configured to capture exo-endocervical cells.

Another embodiment of the present invention provides a method of simultaneously collecting exocervical and endocervical cells from a female patient. The method includes providing a combination exo-endocervical sampling device including a sampler having a pair of opposing wings and a prominence extending from the wings, at least one of the opposing wings and the prominence including a multiplicity of looped fibers defining a void space therebetween configured to capture exo-endocervical cells. The method additionally includes placing the sampling device in contact with a cervix of the female patient. The method further includes collecting exocervical cells with the opposing wings of the sampling device, and simultaneously collecting endocervical cells with the prominence.

BRIEF DESCRIPTION OF THE DRAWINGS

Embodiments of the invention are better understood with reference to the following drawings. The elements of the drawings are not necessarily to scale relative to each other. Like reference numerals designate corresponding similar parts.

FIG. 1C illustrates a top view of a combination exo-endocervical sampler according to one embodiment of the present invention.

FIG. 2 illustrates a perspective view of a brush portion of a combination exo-endocervical sampler according to one embodiment of the present invention.

FIG. 3A illustrates a cross-sectional view of a fiber of the brush portion illustrated in FIG. 2.

FIG. 3B illustrates a cross-sectional view of another fiber for the brush portion illustrated in FIG. 2 according to one embodiment of the present invention.

FIG. 6 illustrates a front view of another combination exo-endocervical sampler according to one embodiment of the present invention.

FIG. 7 illustrates a front view of another combination exo-endocervical sampler according to one embodiment of the present invention.

FIG. 8 illustrates a perspective view of another brush portion of a combination exo-endocervical sampler according to one embodiment of the present invention.

DETAILED DESCRIPTION

In the following Detailed Description, reference is made to the accompanying drawings which form a part hereof, and in which is shown by way of illustration specific embodiments in which the invention may be practiced. In this regard, directional terminology, such as "top," "bottom," "front," "back," "leading," "trailing," etc., is used with reference to the orientation of the Figure(s) being described. Because components of the embodiments can be positioned in a number of different orientations, the directional terminology is used for purposes of illustration and is in no way limiting. It is to be understood that other embodiments may be utilized and structural or logical changes may be made without departing from the scope of the present invention. The following detailed description, therefore, is not to be taken in a limiting sense, and the scope of the present invention is defined by the appended claims.

Figures 1A, 1B:
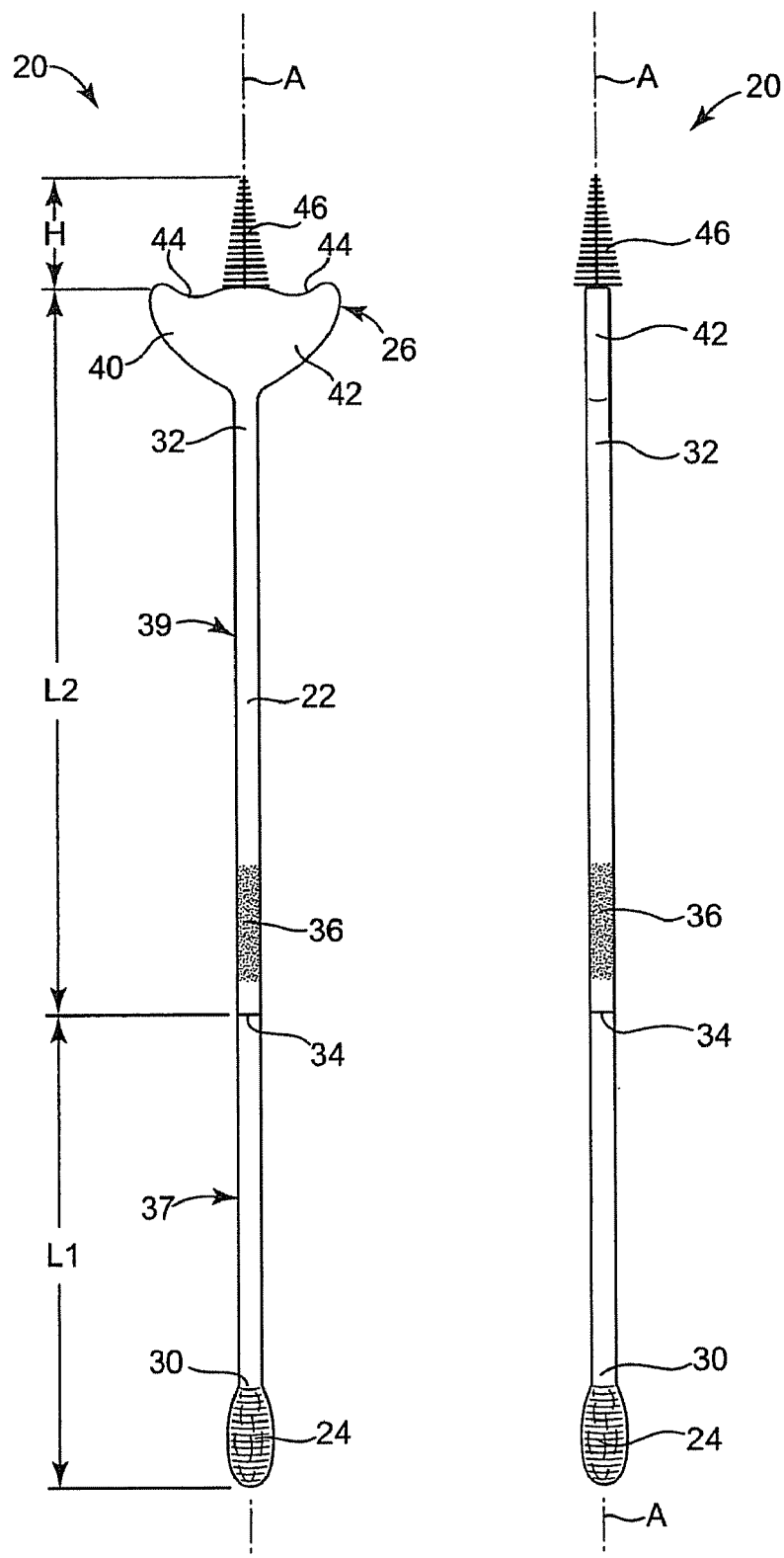
FIG. 1A illustrates a front view of a combination exo-endocervical sampling device according to one embodiment of the present invention.
FIG. 1B illustrates a side view of the combination exo-endocervical sampling device illustrated in FIG. 1A.

FIG. 1A illustrates a front view of a combination exo-endocervical sampling device 20 according to one embodiment of the present invention. Combination exo-endocervical sampling device 20 includes a shaft 22, a sampler 24, and a combination exo-endocervical sampler 26. As a point of reference, shaft 22 and sampling device 20 are aligned along a central axis A. Central axis A is a major, or longitudinal, axis of sampling device 20.

Although combination exo-endocervical sampling device 20 is not typically employed in a sterile field when cell samples are collected, one embodiment provides for combination exo-endocervical sampling device 20 to be sterilized or sterilizable. In any regard, combination exo-endocervical sampling device 20 is provided with a reduced bio-load that does not disrupt cell sampling or analysis.

Shaft 22 defines a first end 30 opposite a second end 32, a transverse break line 34 between the first end 30 and the second 32, and a textured surface 36 adjacent to break line 34. In one embodiment, shaft 22 is integrally formed of molded plastic. Suitable molded plastics for shaft 22 include thermoplastic materials in general, and medical grade polyolefins including polypropylene and polyethylene in particular.

In one embodiment, shaft 22 defines a first portion 37 that extends from break line 34 to sampler 24, and a second portion 39 that extends from break line 34 to combination exo-endocervical sampler 26. In one embodiment, textured surface 36 is disposed on second portion 39 adjacent to break line 34. In this regard, when shaft 22 is severed at break line 34, sampler 24 defines a distal end of first portion 37. In a similar manner, when shaft 22 is severed at break line 34, combination exo-endocervical sampler 26 defines a distal end of second portion 39. In one embodiment, break line 34 is approximately centered within textured surface 36.

In one embodiment, first portion 37 defines a length L1 between about 5 to 7 cm, and preferably the length L1 of first portion 37 is about 6.5 cm. In one embodiment, second portion 39 defines a length L2 that is between about 16 to 20 cm, preferably about 18 cm.

Figure 4:
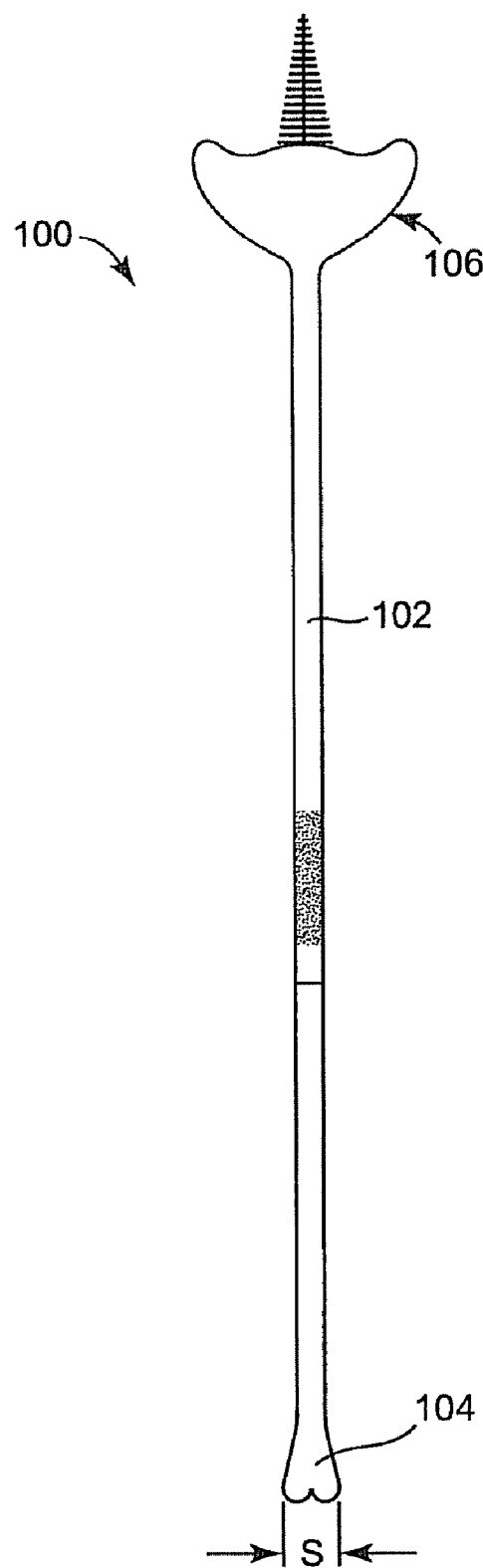
FIG. 4 illustrates a front view of another combination exo-endocervical sampling device according to one embodiment of the present invention.

Sampler 24 is coupled to first end 30. In one embodiment, sampler 24 includes a cotton-tipped swab. In another embodiment, sampler 24 is a rigid spatula (as best illustrated in FIG. 4).

Combination exo-endocervical sampler 26 is coupled to second end 32 of shaft 22. Combination exo-endocervical sampler 26 includes a pair of opposing wings 40, 42 that are disposed transverse to shaft 22 (i.e., transverse to central axis A), and a brush 46 that extends away from the wings 40, 42 along the central axis A of shaft 22. The wings 40, 42 combine to define a generally curved sampling surface 44 separate from a sampling surface area provided by brush 46.

In one embodiment, brush 46 defines a height H between about 1 to 3 cm, and preferably the height H of brush 46 is about 1.5 cm when sampling device 20 is employed in a Pap test on a non-parous patient, and height H of brush 46 is about 2 cm when sampling device 20 is employed in a Pap test for a parous patient.

The sampler 24 and the combination exo-endocervical sampler 26 of the combination exo-endocervical sampling device 20 enable the simultaneous collection of cells during Pap test procedures and wet prep procedures through the use of a single device 20.

As employed herein, parous means a patient who has given birth vaginally one or more times. The terms non-parous and nulli-parous mean a woman who has never given birth vaginally. Pregnant means a patient carrying developing offspring within the body, and in particular within the uterus. Stenotic means a constriction or narrowing of a canal and in particular, a constriction or narrowing of the cervical canal.

FIG. 1B illustrates a right side view of combination exo-endocervical sampling device 20 according to one embodiment of the present invention. In one embodiment, at least a portion of brush 46 defines a diameter that is wider than a thickness of wing 42. In other words, portions of brush 46 extend transverse to the central axis A and are wider than the wings 40, 42 are thick.

FIG. 1C illustrates a top view of exo-endocervical sampler 26 according to one embodiment of the present invention. In one embodiment, exo-endocervical sampler 26 includes rigid, molded wings 40, 42 and a flexible brush 46 formed from looped fibers (as best illustrated in FIG. 2). Wings 40, 42 define a thickness T that is between about 1.5 to 5 mm, and preferably thickness T is between about 2 to 4 mm. In one embodiment, wings 40, 42 extend transverse to the central axis A (FIG. 1A) and combine to define sampling surface 44. Wings 40, 42 are molded from a plastic, such as thermoplastic polyolefin including polyethylene, polypropylene, polyester, nylon, or "soft" polymers including block co-polymers such as block co-polyesters. In general, wings 40, 42 are molded from plastics that are FDA approved for medical devices.

Sampling surface 44 is provided to atraumatically scrape a face portion of a cervix to collect exocervical cells. In one embodiment, sampling surface 44 includes an array of beads 60a, 60b, 60c, 60d, 60e, 60f that project from sampling surface 44 by between about 1-2 mm. In one embodiment, the array of beads 60a, 60b, 60c, 60d, 60e, 60f is a staggered array of alternating beads, as illustrated. As shown in the illustrated embodiment, the sampling surface 44 has a first row of first projections (e.g., beads in the top row in FIG. 1C including beads 60b and 60d) with each of the first projections spaced one from a next by a gap and a second row of second projections (e.g., beads in the bottom row in FIG. 1C including beads 60a, 60c, 60e, and 60f) with each of the second projections spaced apart and disposed in one of the gaps formed by the first row of first projections. It is to be understood that other patterns of arranging 60a, 60b, 60c, 60d, 60e, 60f are also acceptable, and other suitable arrangements of beads is contemplated. In addition, although beads 60a, 60b, 60c, 60d, 60e, 60f are illustrated as circular, other shapes and conformations of beads 60a, 60b, 60c, 60d, 60e, 60f are contemplated. Sampling surface 44 and beads 60a, 60b, 60c, 60d, 60e, 60f combine to atraumatically collect, or sample, exocervical cells during a Pap test procedure.

FIG. 2 illustrates a perspective, simplified view of brush 46 according to one embodiment of the present invention. In general, brush 46 is provided to atraumatically collect endocervical cell samples. Brush 46 includes multiple loops of fibers 70, only three of which are illustrated in the simplified view. It is to be understood that brush 46 includes many multiples of loops of fibers 70. In this regard, in one embodiment the multiple loops of fibers 70 are wound in a helical fashion. In another embodiment, the multiple loops of fibers 70 are wound and uniformly spaced in a symmetric "Christmas tree" configuration. In any regard, the loops of fibers 70 do not terminate in an end, as is commonly associated with a bristle of a bristle-styled brush. Bristles of a bristle brush have the potential to damage cells as they are collected. In contrast, the endless loops of fibers 70 atraumatically collect exo-endocervical and retain the cells in a void space defined between the loops of fibers 70.

Brush 46 includes a semi-rigid or rigid strand 68, and looped fibers 70a, 70b, and 70c that are coupled to strand 68. Strand 68 is generally oriented along central axis A, and looped fibers 70a, 70b, and 70c generally extend transverse to strand 68 and central axis A. In one embodiment, strand 68 includes two twined or twisted strands wrapped to capture looped fibers 70a, 70b, and 70c. Strand 68 includes corrosion resistant metal, such as stainless steel. Alternatively, strand 68 is formed from plastic materials, such as nylon or polyester. In one embodiment, each looped fiber includes a first closed end 72 opposite a second closed end 74, and the closed ends 72, 74 extend transverse from the central axis A.

The open spaces between the closed loop ends 72, 74 provide a first means to atraumatically collect endocervical cell samples. Looped fibers 70a, 70b, and 70c capture and retain cervical cell samples between loop ends 72, 74. In contrast to the known bristle brushes that have bristle ends (i.e. end-on bristles), looped fibers 70a, 70b, and 70c do not have bristle ends that can potentially puncture or otherwise damage tissue. Significantly, looped fibers 70a, 70b, and 70c are provided with closed loop ends 72, 74 that present a lower puncture/trauma risk to tissue when compared to end-on bristles of the known cervical brushes.

FIG. 3A illustrates a cross-sectional view of looped fiber 70a according to one embodiment of the present invention. In one embodiment, looped fiber 70a defines a transverse cross-section that is tri-lobal. For example, looped fiber 70a includes a first lobe 80a, a second lobe 80b, and a third lobe 80c.

In one embodiment, looped fiber 70a defines an effective diameter D1 of between about 50 micrometers (microns) to about 1,000 microns. Diameter and effective diameter are terms that are used broadly in this Specification to define the outermost planform (or perimeter) of an object viewed in cross-section. Diameter, as used herein, is not limited to circular objects. In particular, shaped looped fibers, such as fiber 70a, define a perimeter that is non-circular.

The open area between each lobe 80a, 80b, 80c defines a trough that is suitable for the atraumatic collection of cervical cells. Looped fiber 70a defines a non-circular perimeter in transverse cross-section that is configured for atraumatic collection of cervical cells in a Pap test procedure. In this regard, the surfaces of looped fiber 70a are suited to abrade portions of the endocervical canal to remove cervical cells for sampling without traumatizing the surface from which the cells are removed, and without damaging the collected cells. The cross-sectional non-circular shape of looped fibers 70 provide a second means for atraumatically collecting endocervical cell samples.

Suitable fibers and equipment to produce suitable fibers are available from, for example, Hills, Inc., W. Melbourne, Fla. Other suitable fibers are shaped fibers available from Du Pont, Wilmington, Del. One such suitable fiber is a mushroom-shaped bicomponent fiber identified as a 3GT fiber available from Du Pont-Torray Co., as marketed by Du Pont-Torray Co., Ltd., and available through Du Pont in Wilmington, Del.

FIG. 3B illustrates a cross-sectional view of another looped fiber 70a. In one embodiment, looped fiber 70a is X-shaped in transverse cross-section. In another embodiment, looped fiber 70a is cross-shaped in transverse cross-section. In this regard, X-shaped looped fiber 70a defines an effective diameter D2 that is between about 50 to 1,000 microns. The open areas illustrated between legs of the X-shaped fiber 70a form troughs that are suitable for atraumatic collection of cervical cells in a Pap test procedure, as described above.

Suitable materials for forming/extruding shaped looped fibers 70 include polyolefins in general and thermoplastic polymers such as nylon, or polyester in particular.

FIG. 4 illustrates a front view of another combination exo-endocervical sampling device 100 according to one embodiment of the present invention. Combination exo-endocervical sampling device includes a shaft 102, a sampler 104, and a combination exo-endocervical sampler 106. In general, shaft 102 and exo-endocervical sampler 106 are similar to shaft 22 and exo-endocervical sampler 26, respectively, illustrated in FIG. 1A above.

In one embodiment, sampler 104 includes a molded plastic spatula that defines a width S of between about 0.5 to 2 cm, and preferably width S is about 0.75 cm. In one embodiment, molded plastic spatula sampler 104 is integrally formed with shaft 102 of a molded plastic, such as, for example, polyethylene. Sampler 104 is suitable for atraumatic collection of cervical cells from a face of a cervix and/or cells from a vaginal wall, for example, during a Pap test procedure.

Figures 5A, 5B:
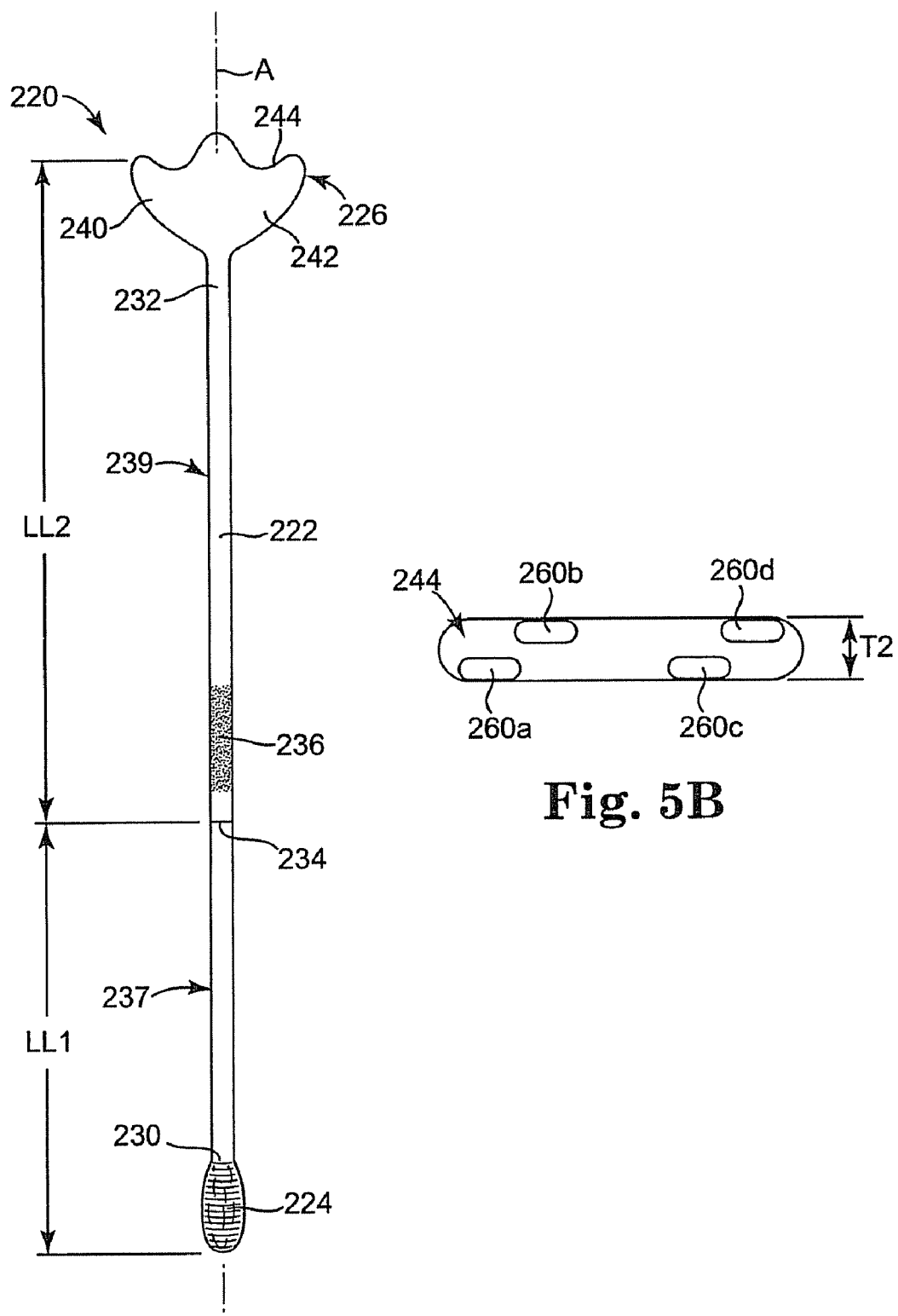
FIG. 5A illustrates a front view of an exocervical sampling device according to one embodiment of the present invention.
FIG. 5B illustrates a top view of one end of the exocervical sampling device illustrated in FIG. 5A.

FIG. 5A illustrates a front view of an exocervical sampling device 220 according to one embodiment of the present invention. In one embodiment, exocervical sampling device 220 is configured for cervical cell sampling of a pregnant patient and includes a shaft 222, a sampler 224, and an exocervical sampler 226. In one embodiment, exocervical sampling device 220 is sterilized or sterilizable, similar to device 20 above.

Shaft 222 defines a first end 230 opposite a second end 232, a transverse break line 234 between the first end 230 and the second 232, and a textured surface 236 adjacent to break line 234. In one embodiment, shaft 222 is integrally formed of molded plastic. Suitable molded plastics for shaft 222 include thermoplastic materials in general, and medical grade plastics including polypropylene and polyethylene in particular.

In one embodiment, shaft 222 defines a first portion 237 that extends from break line 234 to sampler 224, and a second portion 239 that extends from break line 234 to combination exo-endocervical sampler 226. In one embodiment, textured surface 236 is disposed on second portion 239 adjacent to break line 234. In this regard, when shaft 222 is severed at break line 234, sampler 224 defines a distal end of first portion 237. In a similar manner, when shaft 222 is severed at break line 234, combination exo-endocervical sampler 226 defines a distal end of second portion 239. In another embodiment, textured surface 236 spans either side of break line 234.

In one embodiment, first portion 237 defines a length LL1 between about 5 to 7 cm, and preferably the length LL1 of first portion 237 is about 6.5 cm. In one embodiment, second portion 239 defines a length LL2 that is between about 16 to 20 cm, preferably about 16.5 cm.

Sampler 224 is coupled to first end 230. In one embodiment, sampler 224 is a mat of fibers, such as are provided in a cotton-tipped swab. In another embodiment, sampler 224 is a rigid spatula (similar to spatula 104 illustrated in FIG. 4).

Exocervical sampler 226 is coupled to second end 232 of shaft 222. Exocervical sampler 226 includes a pair of opposing wings 240, 242 that are disposed transverse to shaft 222 (i.e., transverse to central axis A) and are curved to correspond to a shape compatible with an exterior surface of the cervix. The wings 240, 242 combine to define a sampling surface 244.

FIG. 5B illustrates a top view of exocervical sampler 226 according to one embodiment of the present invention. Wings 240, 242 define a thickness T2 that is between about 1.5 to 5 mm, and preferably thickness T2 is between about 2 to 4 mm. In one embodiment, wings 240, 242 extend transverse to the central axis A (FIG. 1A) and combine to define sampling surface 244.

Sampling surface 244 is provided to atraumatically scrape a face portion of a cervix of a pregnant patient to collect exocervical cells. In one embodiment, sampling surface 244 includes an array of beads 260a, 260b, 260c, 260d that project above sampling surface 244. In one embodiment, array of beads 260a, 260b, 260c, 260d is a staggered array, although other arrangements for beads 260a, 260b, 260c, 260d are also acceptable. Beads 260a, 260b, 260c, 260d are illustrated as cylinders, although other shapes are also acceptable. Sampling surface 244 and beads 260a, 260b, 260c, 260d combine to atraumatically collect, or sample, exocervical cells from a face of a cervix of a pregnant patient during a Pap test procedure.

In one embodiment, wings 240, 242 are molded from a plastic, such as thermoplastic polymers including polyethylene, polypropylene, polyester, nylon, or "soft" polymers including block co-polymers such as block co-polyesters. In general, wings 240, 242 are molded from plastics that are FDA approved for medical devices.

In another embodiment, wings 240, 242 include a lofted intertwined mat of endless fibers that form a surface that is characterized by a random collection of interconnecting fibrils, as more fully described below in FIG. 9A.

FIG. 6 illustrates a front view of another combination exo-endocervical sampler 326 according to one embodiment of the present invention. Combination exo-endocervical sampler 326 includes a pair of opposing wings 340, 342 that are disposed transverse to shaft 322 (i.e., transverse to central axis A), and a brush 346 that extends away from the wings 340, 342 along the central axis A of shaft 322. The wings 340, 342 combine to define a sampling surface 344 separate from a sampling surface area provided by brush 346.

In one embodiment, brush 346 is substantially cylindrical in shape and defines a height H2 between about 1 to 3 cm, and preferably the height H2 of brush 346 is about 1.5 cm when sampler 326 is employed in a Pap test on a non-parous patient, and height H2 of brush 346 is about 2 cm when sampler 326 is employed in a Pap test for a parous patient.

Brush 346 includes multiple loops of fibers 370. Brush 346 includes a semi-rigid or rigid strand 368, and looped fibers 370 that are coupled to strand 368. Strand 368 is generally oriented along central axis A, and looped fibers 370 generally extend transverse to strand 368 and central axis A. In one embodiment, strand 368 includes two twined or twisted strands wrapped to capture looped fibers 370.

Strand 368 includes corrosion resistant metal, such as stainless steel. Alternatively, strand 368 is formed from plastic materials, such as nylon. In one embodiment, each looped fiber includes a first closed end opposite a second closed end, and the closed ends extend transverse from the central axis A, in a manner similar to that illustrated in FIG. 2.

Fibers 370 are similar to the fibers illustrated in FIGS. 2 and 3A and 3B. In this regard, fibers 370 are looped and can include a non-circular perimeter in transverse cross-section that is configured for atraumatic collection of cervical cells in a Pap test procedure. Looped fibers 370 are suited to abrade portions of the endocervical canal to remove cervical cells for sampling without traumatizing the surface from which the cells are removed.

FIG. 7 illustrates a front view of another embodiment of a combination exo-endocervical sampler 426 according to one embodiment of the present invention. Combination exo-endocervical sampler 426 includes a pair of opposing wings 440, 442 that are disposed transverse to shaft 422 (i.e., transverse to central axis A), and a brush 446 that extends away from the wings 440, 442 along the central axis A of shaft 422. The wings 440, 442 combine to define a sampling surface 444 separate from a sampling surface area provided by brush 446.

In one embodiment, brush 446 is substantially conical in shape and defines a height H3 between about 1 to 3 cm, and preferably the height H3 of brush 446 is about 1.5 cm when sampler 426 is employed in a Pap test on a non-parous patient, and height H3 of brush 446 is about 2 cm when sampler 426 is employed in a Pap test for a parous patient.

Brush 446 includes multiple loops of fibers 470 wound conically in a helical fashion about a semi-rigid or rigid strand 468. Strand 468 is generally oriented along central axis A, and looped fibers 470 generally extend transverse to strand 468 and central axis A. In one embodiment, strand 468 includes two twined or twisted strands wrapped to capture looped fibers 470.

Strand 468 includes corrosion resistant metal, such as stainless steel. Alternatively, strand 468 is formed from plastic materials, such as nylon. In one embodiment, each looped fiber includes a first closed end opposite a second closed end, and the closed ends extend transverse from the central axis A, in a manner similar to that illustrated in FIG. 2.

Fibers 470 are similar to the fibers illustrated in FIGS. 2 and 3A and 3B. In this regard, fibers 470 are looped and can include a non-circular perimeter in transverse cross-section that is configured for atraumatic collection of cervical cells in a Pap test procedure. Looped fibers 470 are suited to abrade portions of the endocervical canal to remove cervical cells for sampling without traumatizing the surface from which the cells are removed.

FIG. 8 illustrates a perspective view of a brush 546 according to one embodiment of the present invention. Brush 546 is usefully employed on any one of the combination exo-endocervical samplers 26, 106, 326, and 426 illustrated above.

In one embodiment, brush 546 is substantially conical in shape and defines a height H4 between about 1 to 3 cm, and preferably the height H4 of brush 546 is about 1.5 cm when employed in a Pap test on a non-parous patient, and height H4 of brush 546 is about 2 cm when employed in a Pap test for a parous patient.

Brush 546 includes a sponge 550 that defines a helical surface 552 wound about a semi-rigid or rigid strand 568. In one embodiment, sponge 550 is an open celled absorbent sponge formed of natural or synthetic cellulose or its derivatives, or of polymers. In another embodiment, sponge 550 is a closed cell sponge form of polyurethane or the like. Strand 568 is generally oriented along central axis A, and includes corrosion resistant metal, such as stainless steel. Alternatively, strand 568 is formed from plastic materials, such as nylon.

Helical surface 552 includes helically spaced ledges 554*a*, 554*b*, and 554*c*. Helical surface 552 is suited to abrade portions of the endocervical canal to remove cervical cells for sampling without traumatizing the surface from which the cells are removed.

In one embodiment, brush 546 includes a pair of opposing wings defined by helical surfaces 552 that are disposed transverse to the strand 568, and a prominence defined by top 550 of sponge. Prominence, or top 550 of sponge, extends from the wings 552 along a central axis A of the strand 568. In this regard, the opposing wings 552 define a first sampling surface and the prominence 550 defines a second sampling surface. The sponge 550 is characterized by an absence of bristles and defines pores or a void space within the sponge 550 that is configured to capture exo-endocervical cells.

Figure 9A:
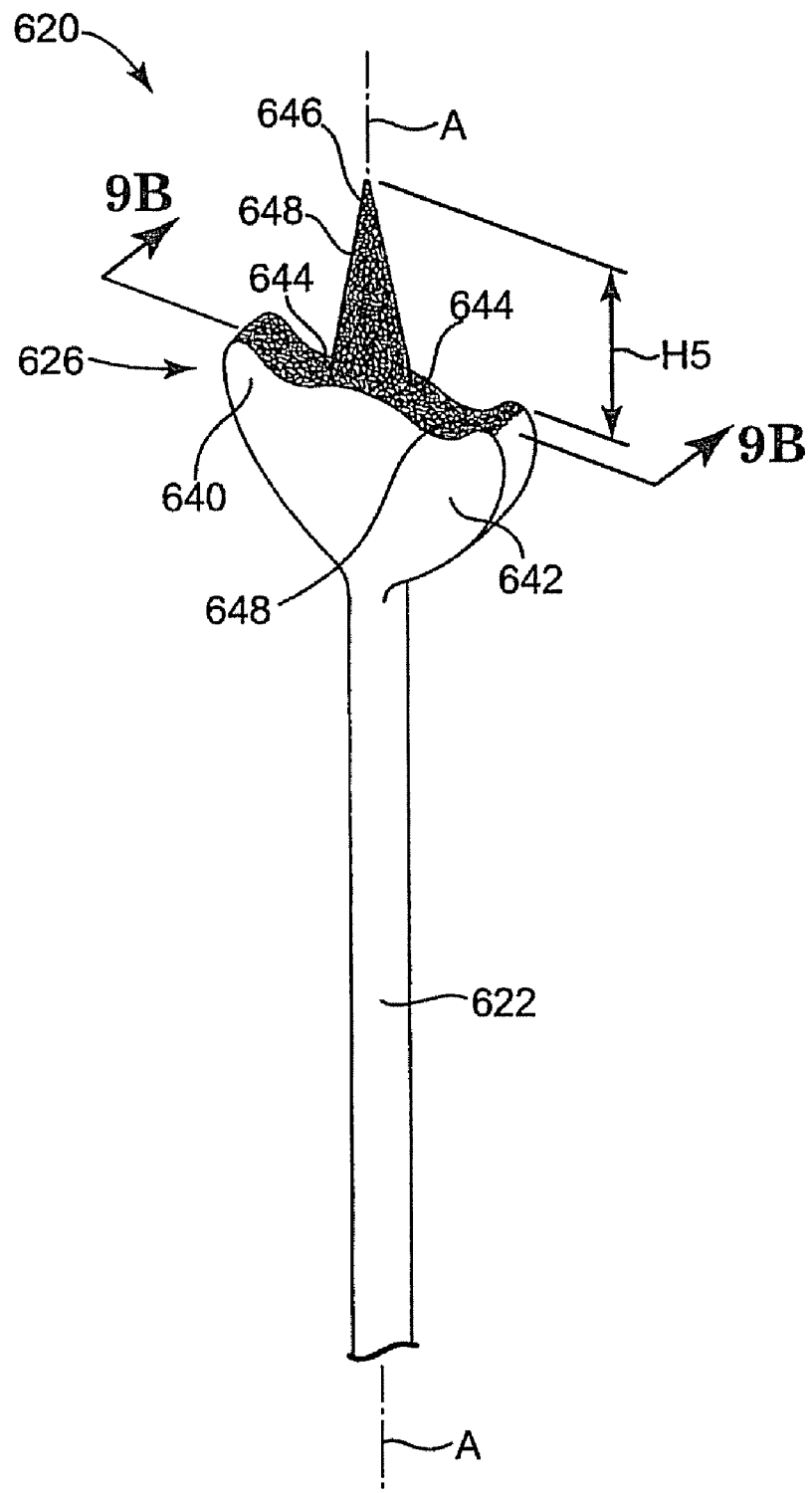
FIG. 9A illustrates a perspective view of another combination exo-endocervical sampling device according to one embodiment of the present invention.

FIG. 9A illustrates a perspective view of another combination exo-endocervical sampling device 620 according to one embodiment of the present invention. Combination exo-endocervical sampling device 620 includes a shaft 622, and a combination exo-endocervical sampler 626 extending from shaft 622 and aligned along a central longitudinal axis A. In one embodiment, a separate sampler such as a swab or a spatula is coupled to shaft 622 opposite sampler 626 in a manner similar to that illustrated in FIG. 1A (swab) or FIG. 4 (spatula).

Combination exo-endocervical sampler 626 includes a pair of opposing wings 640, 642 that are disposed transverse to shaft 622 (i.e., transverse to central axis A), and a prominence 646 that extends away from the wings 640, 642 along the central axis A of shaft 622. The prominence 646 and wings 640, 642 combine to define a sampling surface 644. In one embodiment, sampling surface 644 is covered at least partially by a lofted intertwined mat 648 of looped fibers that is suitable for the collection of cells from the cervical face and/or the endocervical canal.

In one embodiment, prominence 646 is substantially conical in shape and defines a height H5 between about 1 to 3 cm, and preferably the height H5 of prominence 646 is about 1.5 cm when sampler 626 is employed in a Pap test on a non-parous patient, and height H5 of prominence 646 is about 2 cm when sampler 626 is employed in a Pap test for a parous patient.

Lofted intertwined mat 648 of fibers forms a surface that is characterized by a random collection of interconnecting fibrils. The interconnecting fibrils define open spaces between the fibrils. The fibrils and the opens spaces combine to create a "lofty" structure that is useful in the atraumatic collection of cervical cells in a Pap test procedure. The looped fibrils may be referred to as "endless" fibers or fibrils, as individual fibrils forming the lofted intertwined mat 648 are formed to have no distinct "beginning" or "end" (i.e., the fibrils are not bristles). The lofted intertwined mat 648 is suited to abrade portions of the endocervical canal to remove cervical cells for sampling, and the open spaces between fibrils gather/retain the cells and minimize trauma to the cells as the cells are removed from the patient.

Figure 9B:
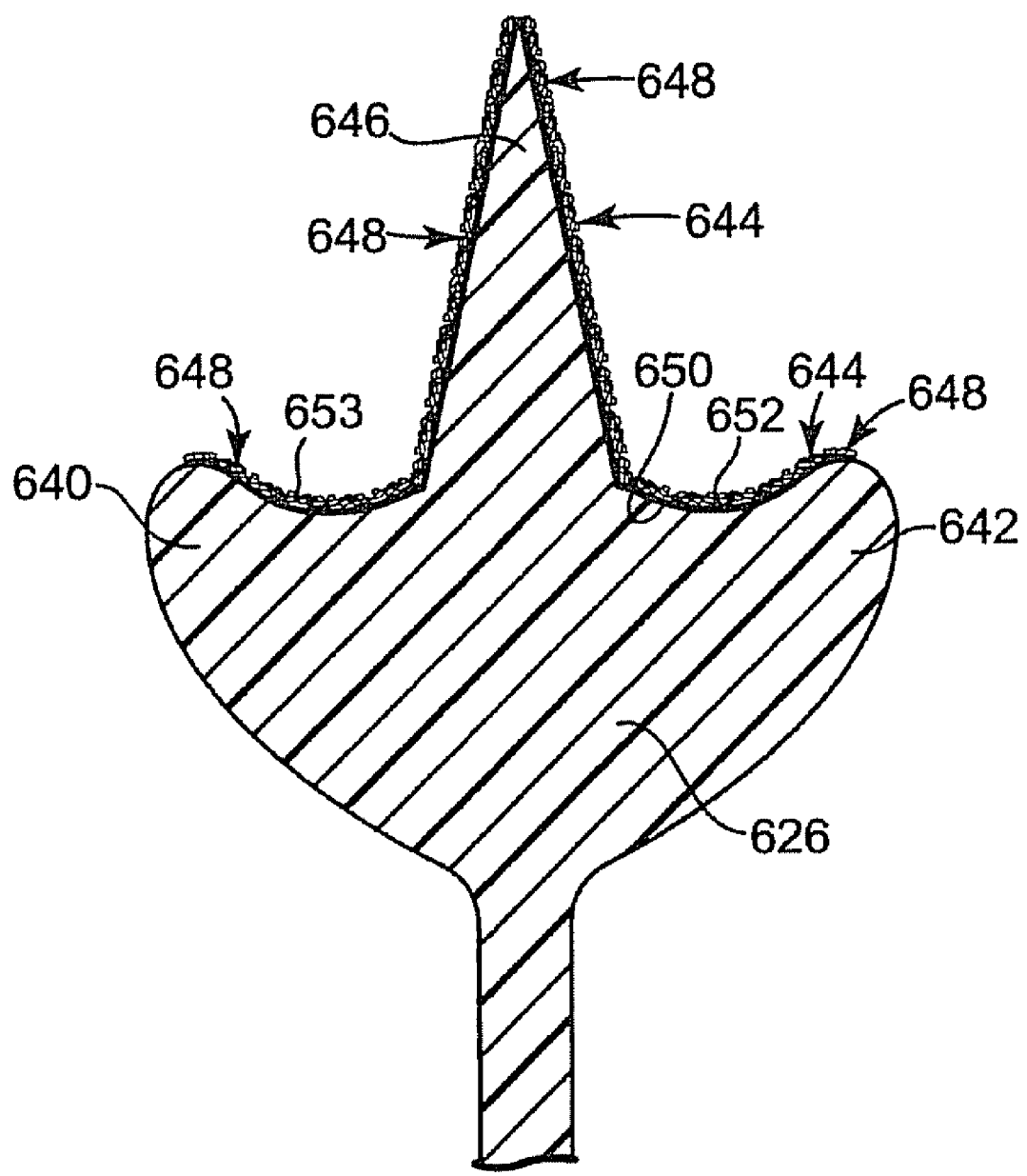
FIG. 9B illustrates a cross-sectional view of a combination exo-endocervical sampler of the device illustrated in FIG. 9A.

FIG. 9B illustrates a cross-sectional view of combination exo-endocervical sampler 626. Wings 640, 642 and prominence 646 are covered by lofted intertwined mat 648 of fibers. In one embodiment, lofted intertwined mat 648 of fibers includes a base 650 and intertwined fibers 652 extending from base 650. In one embodiment, lofted intertwined mat 648 of fibers is formed by extruding fibers 652 from a strand die onto a carrier web, or base 650. In an alternative embodiment, lofted intertwined mat 648 of fibers is formed by extruding fibers 652 from a strand die onto a moving conveyor belt, where the speed of the conveyor belt is selected to enable a portion of fibers 652 to cool into a continuous polymeric base 650, and another portion of fibers 652 becomes randomly tangled and intertwined as they cool on top of base 650. In this manner, a single process is employed to form base 650 and intertwine fibers 652. By an appropriate selection of fiber extrusion rate and collection speed, the mat of randomly intertwined fibers 652 will extend a distance from base 650 to provide a lofty structure. Between each of the randomly intertwined fibers 652, a void or space 653 is defined that is suited for the collection of cervical cell samples.

In one embodiment, base 650 and intertwined fibers 652 are formed from a thermoplastic polymeric material. Preferably, thermoplastic polymeric material is flexible, soft, and suited for medical applications. Examples of suitable thermoplastic materials include polyurethane, polyolefins, and polyolefins including a soft fraction of another polymer, for example, polybutylene. In one embodiment, after forming base 650 and intertwined fiber 652, lofted intertwined mat 648 of "endless" fibers is thermo-formed onto sampler 626 to cover wings 640, 642 and prominence 646.

Figure 10:
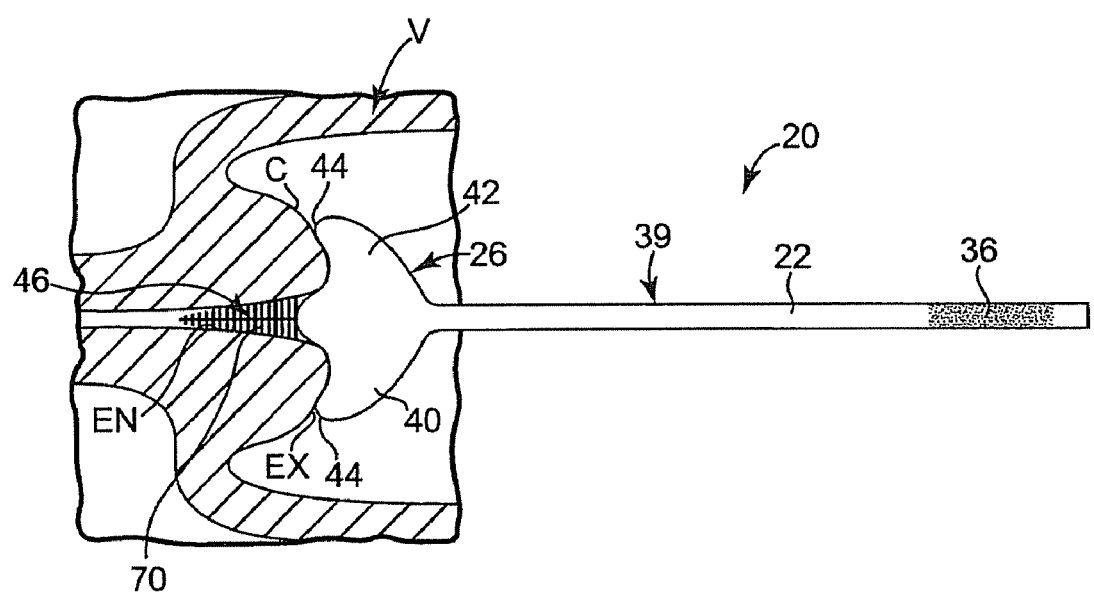
FIG. 10 illustrates a cross-sectional view of a combination exo-endocervical sampling device employed to simultaneously collect exocervical and endocervical cells.

FIG. 10 illustrates a cross-sectional view of combination exo-endocervical sampling device 20 employed to collect cervical cells from a cervix during a Pap test according to one embodiment of the present invention.

With reference to FIG. 1A, second portion 39 of combination exo-endocervical sampling device 20 has been severed from first portion 37. First portion 37 including sampler 24 (FIG. 1A) is provided to permit the clinician to collect a sample of cells from a wall of vagina V. Generally, sampler 24 is swabbed along walls of the vagina V to capture cells for analysis. First portion 37 having the cells collected on sampler 24 is removed from the vagina V, deposited inside a standard sized test tube, the test tube is capped, and the collected sample is sent to a laboratory for analysis.

Thereafter, second portion 39 is inserted into the vagina V to collect cervical cells. For example, exo-endocervical sampler 26 is placed in contact with the cervix C such that sampling surface 44 contacts exocervical surface EX and brush 46 enters the cervical os to contact endocervical surface EN.

Textured surface 36 on shaft 22 is available to provide a gripping surface that enables a clinician, for example a clinician wearing gloves, to rotate shaft 22. Rotation of shaft 22 rotates exo-endocervical sampler 26 such that sampling surface 44 sweeps across the exocervical surface EX and brush 46 rotates within and around the endocervical surface EN. In this manner, sampling surface 44 collects cells from exocervical surface EX and looped fibers 70 atraumatically abrades and collects cells from the endocervical surface EN of cervix C. The exo-endocervical cells that are collected are appropriately "smeared" across one or more microscope plates and readied for subsequent laboratory analysis, or alternatively, deposited in a standard wet prep broth container.

In one embodiment, combination exo-endocervical sampling devices described above are selected based upon a status of the patient. For example, one algorithm of use provides that the clinician determines whether the patient is pregnant, and if so selects exocervical sampling device 200 (FIG. 5A). If the patient is not pregnant, the clinician determines if the patient is nulli-parous and/or likely stenotic, and if so employs combination exo-endocervical sampling device 20 (FIG. 1A). In this regard, in the case where the patient is nulli-parous, height H of brush 46 is selected to have a height of about 1.5 cm. If the clinician determines that the patient is parous, the clinician selects combination exo-endocervical sampling device 20 provided with brush 46 having a height H of about 2.0 cm.

Embodiments described above permit the clinician to use one tool to collect both endocervical and exocervical cell samples during a Pap test procedure. This reduces the duration of the office visit, which translates to improved clinic efficiency, and reduces the cost of the instruments used to collect the samples. The looped fibers effectively collect endocervical cell samples without traumatizing the endocervical tissue or the cells. The combination exo-endocervical sampling devices described above permit the clinician to match the device to a given cervix type and sample tissue, which after analysis and diagnosis provides vitally important information useful to the clinician in the early diagnosis of cytopathologic abnormalities and common vaginoses.

Although specific embodiments have been illustrated and described herein, it will be appreciated by those of ordinary skill in the art that a variety of alternate and/or equivalent implementations may be substituted for the specific embodiments shown and described without departing from the scope of the present invention. This application is intended to cover any adaptations or variations of the specific embodiments discussed herein. Therefore, it is intended that this invention be limited only by the claims and the equivalents thereof.

What is claimed is:

1. A method of simultaneously collecting exocervical and endocervical cells from a female patient, the method comprising:

providing a combination exocervical sampling device including a sampler having a pair of opposing wings and a prominence extending from the wings, the opposing wings comprising a sampling surface and the prominence comprising a multiplicity of endless looped fiber pairs distributed axially along a distal end section of the prominence, each looped fiber pair including a first loop extending transverse from the shaft and a second loop extending transverse from the shaft, the loops defining a void space in each loop configured to capture exocervical cells;

placing the sampling device in contact with a cervix of the female patient;

collecting exocervical cells with the opposing wings of the sampling device; and simultaneously collecting endocervical cells with the prominence.

2. The method of claim 1, wherein each looped fiber pair comprises a continuous figure-eight-shaped looped fiber.

3. The method of claim 1, wherein the opposing wings comprise a staggered array of beads.

\* \* \* \* \*